(12) United States Patent  (10) Patent No.: US 8,331,528 B2
Kayzerman  (45) Date of Patent: Dec. 11, 2012

(54) INTRAORAL X-RAY SYSTEM

(75) Inventor: Boris Kayzerman, Bat Yam (IL)

(73) Assignee: Anatoly Vinogratzki, Bat-yam (IL)

( * ) Notice: Subject to any disclaimer, the term of this patent is extended or adjusted under 35 U.S.C. 154(b) by 0 days.

(21) Appl. No.: 12/442,163

(22) PCT Filed: Sep. 25, 2007

(86) PCT No.: PCT/IL2007/001195
§ 371 (c)(1),
(2), (4) Date: May 4, 2009

(87) PCT Pub. No.: WO2008/038285
PCT Pub. Date: Apr. 3, 2008

(65) Prior Publication Data
US 2010/0074401 A1 Mar. 25, 2010

(30) Foreign Application Priority Data
Sep. 28, 2006 (IL) .......................................... 178393

(51) Int. Cl.
A61B 6/14 (2006.01)
(52) U.S. Cl. ......................................... 378/38; 378/168
(58) Field of Classification Search .................. 378/167, 378/168, 169
See application file for complete search history.

(56) References Cited

U.S. PATENT DOCUMENTS

| 2,476,776 | A | | 7/1947 | Smathers |
| 3,622,785 | A | | 11/1971 | Irwin et al. |
| 6,652,141 | B1 | * | 11/2003 | Cianciosi ...................... 378/191 |
| 2004/0066898 | A1 | * | 4/2004 | Schick et al. ................ 378/98.9 |
| 2005/0226389 | A1 | | 10/2005 | Yoon et al. |
| 2006/0262461 | A1 | * | 11/2006 | Wood ................................ 361/1 |
| 2007/0053498 | A1 | * | 3/2007 | Mandelkern et al. ......... 378/184 |

FOREIGN PATENT DOCUMENTS

| EP | 1330982 A2 | 7/2003 |
| EP | 1699232 A2 | 9/2006 |
| JP | 1170443 A | 7/1989 |

* cited by examiner

Primary Examiner — Hoon Song
(74) Attorney, Agent, or Firm — Marsteller & Associates, P.C.

(57) ABSTRACT

An improved intraoral x-ray system that includes a dental tray with the shape of a dental arch and can be positioned within the oral cavity, for accommodating image detectors at the lingual (or, palatal) side of the tray; an image processing system, situated external to said oral cavity, for converting the image data detected by the image detector to a viewable image; a mechanism for transferring the image data to the image processing system; and a display unit for displaying the image.

25 Claims, 9 Drawing Sheets

INTRAORAL X-RAY SYSTEM

FIELD OF THE INVENTION

The present invention relates in general to the field of x-rays. In particular, the present invention relates to dental x-rays. More particularly, the present invention relates to an anatomically designed dental x-ray apparatus for obtaining an intraoral image.

BACKGROUND OF THE INVENTION

Intraoral dental radiology has been utilized by dentists and oral surgeons for many years in order to obtain images of a patient's teeth, mouth and gums to aid in intraoral diagnosis and treatment. In conventional radiology, a photographic film is positioned in a patient's mouth, for instance, behind his teeth, and an x-ray beam is projected through the teeth onto the film. The film is developed in a dark room or using special chemicals to obtain a viewable photographic image of the teeth.

Several drawbacks are associated with the conventional imaging process described above. In particular, the patient is required to bite down on the photographic film holder for a period of time, which can be uncomfortable, and sometimes even painful, for instance, when the photographic film gouges the gums of the patient, and often causes the patient to experience a gag-reflex. Additionally, the developing process is a time consuming and costly process. Moreover, the photographic film, which is essentially a flat plate, is does not fit the curvature of the dental arch without being bent, thereby resulting in distorted exposures, particularly at the edges of the film. Furthermore, in many cases the film does not fit into the mouth of the patient at the desired location, thereby preventing the possibility of obtaining any images at all of particular teeth or at a particular angle.

In recent years, filmless (or, digital) dental radiology has started replacing the conventional methods of intraoral diagnosis and treatment. Although an x-ray beam is still projected through the patient's teeth, an electronic sensor is placed behind the patient's teeth instead of a photographic film.

There are two main types of systems that are typically used in digital dental radiology. The first, known as a Direct Digital Radiography System, utilizes a sensor and a cord connected to a computer and a monitor to display the digital x-ray image thereon. These systems utilize a flat rigid sensor containing a Charge Coupled Device (CCD) covered with radiation sensitive receptors. Quality images or pictures, similar to developed conventional x-rays, appear instantly on the monitor screen. The images can be stored electronically and printed and or transferred electronically if desired. This technology eliminates the need for film and a dark room (and/or chemicals) as well as the need for a time consuming development process. Additionally, since the electronic sensor is much more sensitive to x-rays than is film, the dosage of radiation that is transferred to the patient may be significantly lowered.

However, the sensors utilized in Direct Digital Radiography Systems have complicated electronic circuitry or chips to correct image distortions that occur due to the flat surface of the sensor with respect to the curved dental arch, as well as to convert the image data to readable format prior to transferring to the display device. Therefore, obtaining and operating Direct Digital Radiology equipment is expensive, as it can cost thousands of dollars, which can be prohibitive to many dental practitioners. Furthermore, depending on its size, the hard sensor may not fit in some locations in the oral cavity.

The second main type of digital system, known as an Indirect Digital Radiography System, may be cordless, and utilizes a storage phosphor transfer image plate, which, after scanning, integrates digitally into a computer and displays the image on a monitor. When exposed to a radiation beam the storage phosphor imaging plate holds an image, which is electronically processed via software to produce the digital image. The smaller size and lack of a cord as compared to the direct system, along with the slight flexibility of the plate, make intraoral placement of phosphor plates easier than that of direct system sensors. Additionally, the elimination of the need for film and a dark room (and/or chemicals) as well as the development process saves in development time of the images. As in direct systems, radiation may be reduced significantly compared to conventional x-ray techniques.

Disadvantages associated with indirect systems, relative to direct systems, include the extra time required to scan and erase the plates. Moreover, the equipment required for indirect systems is very costly, particularly the scanner, which is prohibitive to many dental practitioners.

The DenOptix® Photostimulable Phosphor Plate, manufactured by Gendex, utilizes an elastic phosphor plate for indirect dental radiography. The Gendex phosphor is powder-based and is therefore limited in maximum thickness to 0.3 mm, since for higher thicknesses the light scattering during the scanning process becomes too high, and a lot of light is lost. Also, the light scattering reduces the spatial resolution. Moreover, the Gendex product requires an expensive and bulky scanner, costing tens of thousands of dollars.

There have been several attempts to overcome the problems involved with digital radiography, however, each comprise limitation of its own.

U.S. Pat. No. 3,622,785 discloses a fluoroscopic unit suitable for intraoral use. A phosphor coating is deposited on the face at the tip of a curved fiber optic bundle adapted for placement within the mouth. In response to low x-ray radiation, a low-level image is formed. The image is transmitted through the fiber optic bundle to an image intensifier, which amplifies the image to above the visual threshold, and the image is displayed on a monitor. Although the fiber optic bundle is curved, and may be flexible, since the face of the fiber optic bundle tip is flat, distortion of the image will likely occur. However, U.S. Pat. No. 3,622,785 does not recognize this limitation and therefore does not teach any method of correcting the distorted image. Moreover, in U.S. Pat. No. 3,622,785 the practitioner must hold the unit by hand while directing the fiber optic bundle, and thereby be exposed to radiation in the process.

JP 1170443 discloses a dental arch shaped detector connected to a microcomputer for generating an image of the entire jaw. The detector is bitten by the patient, and when the electrodes are brought into contact with the teeth, current flows between the electrodes. When a change in current is detected, the portion of the detector bitten by the teeth sends data to the microcomputer. The device of JP 1170443 comprises complicated electronics, which adds undesirable costs to the purchase and operation of the system.

US 2005/0226389 discloses an anatomically conforming intraoral dental radiographic sensor comprising two abutted imaging planes having an angle of 20-40 degrees between them. According to US 2005/0226389, this arrangement results in significantly more patient comfort than that provided by a single flat plane of equivalent imaging area. Fiduciary elements are situated on the sensor for marking the field of view. Image distortions caused by non-perpendicularity of the illuminating x-ray beam relative to the surface of the radiation detector are corrected by known mathematical calculations. However, in order to correct the distortions, complicated electronics must be provided, which adds undesirable costs to the purchase and operation of the system. In Addition, this patent is directed to correction of mainly vertical distortion.

U.S. Pat. No. 6,652,141 discloses an oral sensor configured to fit close to a target area in an oral cavity. The sensor is a filmless radiography system that transmits data to a preprocessor via a cable, and then to a display device. The sensor comprises a housing having a lower section and an upper section. The upper section is configured with a cable connector which receives the electrical cable that connects to the printed circuit board of the sensing structure. As seen in FIG. 10 of U.S. Pat. No. 6,652,141, the cable connector juts out toward the center of the oral cavity. Moreover, the upper and lower housing sections comprise a substantial thickness, relative to the typical size of the oral cavity, which, when combined with the cable connector create a sizeable object. When situated in the oral cavity, the patient will find such an object disturbing and uncomfortable, similar to the problem that exists in most intraoral products.

It is therefore an object of the present invention to provide an intraoral digital x-ray apparatus, which allows the dental practitioner to obtain digital intraoral images, and overcomes the drawbacks associated with the prior art, including high costs and discomfort.

It is an additional object of the present invention to provide an intraoral digital x-ray apparatus that provides an undistorted image, which therefore does not require expensive and/or complicated electronics to correct a distorted image prior to display.

It is an additional object of the present invention to provide an intraoral digital x-ray apparatus that is comfortably situated in the oral cavity of a patient.

It is an additional object of the present invention to provide an intraoral digital x-ray apparatus that has the shape of at least part of a dental arch.

It is an additional object of the present invention to provide an intraoral digital x-ray apparatus that requires little skill to operate.

It is yet an additional object of the present invention to provide an intraoral digital x-ray apparatus that reduces or eliminates entirely the gag-reflex associated with conventional intraoral x-ray apparatus Additional objects and advantages of the present invention will become apparent as the description proceeds.

SUMMARY OF THE INVENTION

The present invention relates to an improved intraoral x-ray system for minimizing distortion of a detected intraoral image, said apparatus comprising:
a. a dental tray having the shape of at least part of a dental arch, positionable within the oral cavity, for accommodating at least one image detector at the lingual (or palatal) side of the tray;
b. an image processing system for converting the image data detected by said image detector to a viewable image, wherein said image processing system is situated external to said oral cavity;
c. a mechanism for transferring said image data to said image processing system; and,
d. a display unit for displaying said image.

The mechanism for transferring the image data may comprise a fiber optic bundle, wherein one end of the fiber optic bundle is situated in the oral cavity at the lingual (or, palatal) side of the tray, and wherein the tips of the end of an image detector are chosen from any one of the group consisting of phosphor and a scintillator. Optionally, the entire lingual/palatal side of the dental tray comprises the phosphor or scintillator coated tips of the fiber optic bundle. Alternatively, only part of the lingual/palatal side of the dental tray comprises the phosphor or scintillator coated tips of the fiber optic bundle.

The tray preferably further comprises a rotatable optical device for gathering image data from the phosphor or scintillator coated layer and transferring said data to the processing system. The optical device may be chosen from the group consisting of at least one lens; at least one prism; at least one mirror; and, a combination thereof.

Preferably, the mechanism for transferring the image data comprises wireless technology.

The dental tray preferably comprises the lingual surface of a tray in the shape of an entire dental arch.

The dental tray preferably comprises an elongated strip in the shape of an entire dental arch or alternatively in the shape of part of a dental arch. The elongated strip preferably further comprise securing means for securing at the lingual side of the teeth of a patient, wherein the securing means may be at least one hook, at least one clip or adhesive material.

The apparatus of the present invention may further comprise:
a. an image intensifier in optical communication with the fiber optic bundle; and,
b. a device, such as a camera or a CCD element, which is in optical communication with the output of the image intensifier.

According to one embodiment, the system utilizes indirect digital dental radiaography, wherein the at least one image detector is an image storage plate chosen from one of the group consisting of a phosphor; and, a scintillator, or any material having similar qualities thereof. The phosphor material is preferably a polycrystalline phosphor.

One or more image detectors are affixed at the lingual (or, palatal) portion of the dental tray. The dental tray is preferably covered by an opaque covering.

The image processing system comprises a laser scanner.

According to another embodiment of the present invention, the system utilizes direct digital dental radiaography, wherein the at least one image detector is an image storage plate comprising a row of a plurality of CMOS chips, wide field optics and an array of one or more scintillators.

One or more image detectors are affixed at the lingual (or, palatal) portion of the dental tray.

Optionally, the image detector is a conventional film plate.

According to one embodiment, the dental tray is adjustably bendable between a dental arch shape and a straight line. The dental tray comprises sectional components such as dental arch segments for connecting and disconnecting to form a portion of, or an entire dental arch shaped dental tray.

DETAILED DESCRIPTION OF THE PREFERRED EMBODIMENTS

The advent of digital dental radiology has benefited the dental practitioner. Advantages include the elimination of the photographic film, and thus the need for a dark room (and/or chemicals) as well as the development process. However, several drawbacks are associated with such technology, including the cost of obtaining and operating the equipment and lack of comfort to the patient due to the flat rigid sensor, among others. The present invention solves the above problems by providing an intraoral digital x-ray apparatus that may be comfortably situated in the oral cavity, and avoids image distortion when detecting an intraoral image.

Figure 1:
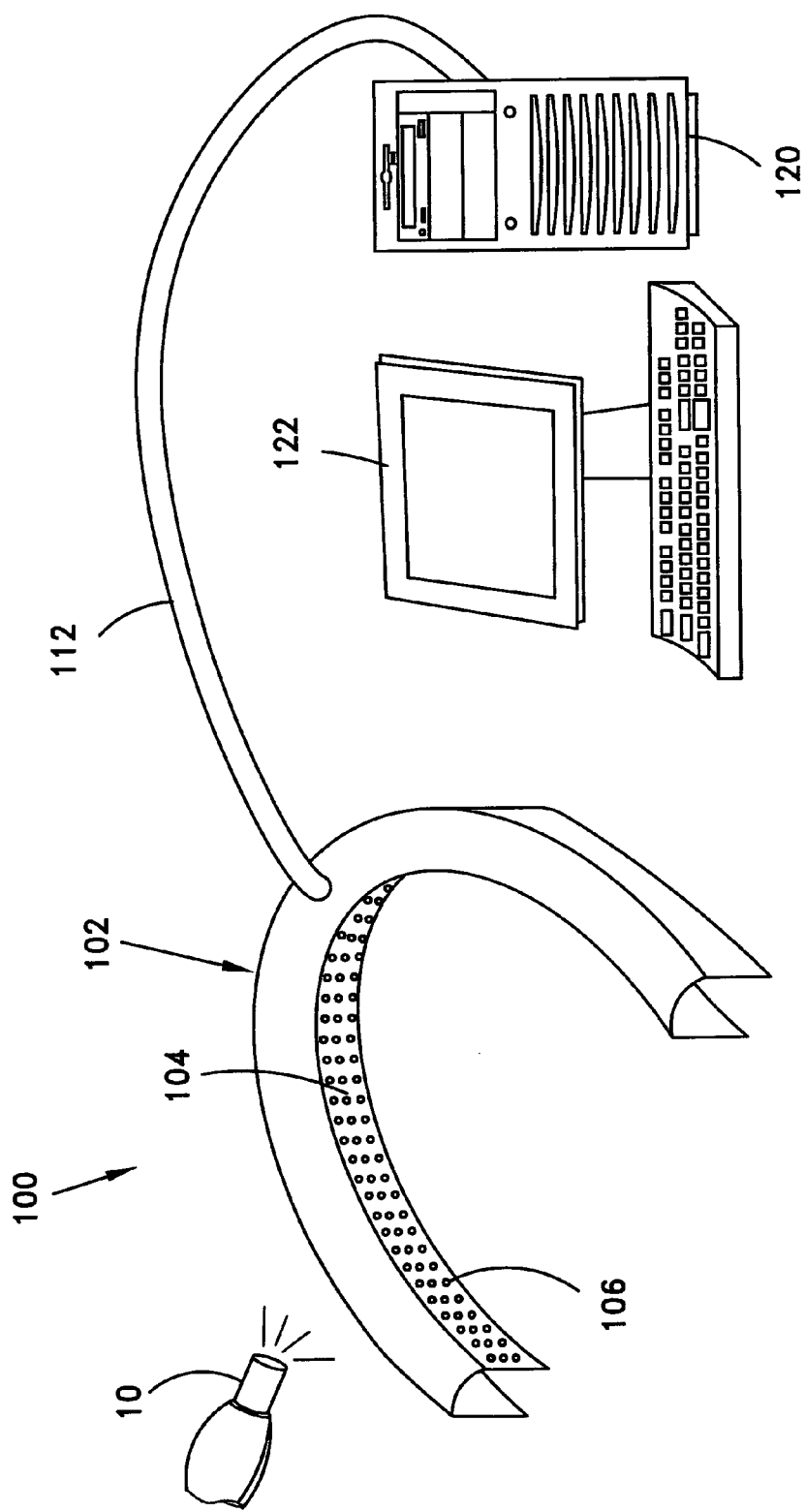
FIG. 1 illustrates a first embodiment of the intraoral digital x-ray apparatus of the present invention wherein an image detector is situated along the entire inner surface of an entire dental tray.

A first embodiment of the intraoral digital x-ray system of the present invention is shown in FIG. 1 and generally designated by the numeral (100). System (100) comprises a dental tray (102) in the shape of an entire dental arch for positioning around the teeth of the lower dental arch of a patient. The inner surface (104) of tray (102) comprises an image detector in the form of a phosphor coated layer (106) extending around the entire length of the arch. Although tray (102) is shown in the figure positionable around the teeth of the lower dental arch, it is understood that tray (102) may be similarly molded to be positioned around teeth of the upper dental arch.

Alternatively, in all embodiments described herein, a scintillator may be used for converting the x-ray radiation into visible light, instead of phosphor.

Figure 2:
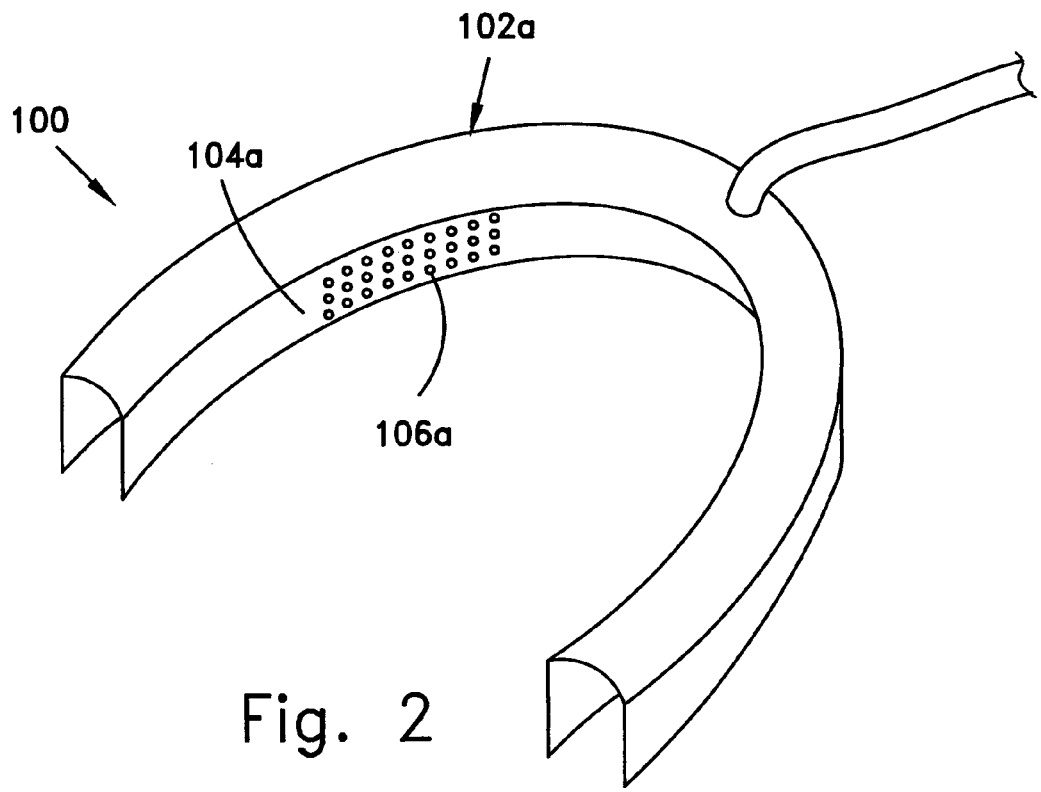
FIG. 2 illustrates the first embodiment of the present invention wherein the image detector is situated along part of the inner surface of the entire dental tray.
Figure 3:
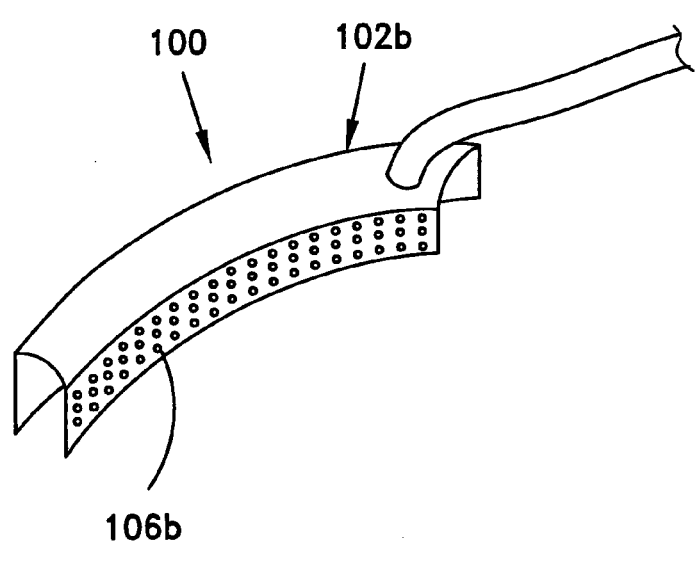
FIG. 3 illustrates the first embodiment of the present invention wherein the image detector is situated along the entire surface of part of a dental tray.

Although tray (102) is shown in FIG. 1 shaped in the form of an entire dental arch, phosphor coated layer (106a) (see FIG. 2) may alternatively comprise only a portion of the length of the dental arch, for obtaining image data of only a few teeth. In this case, several trays are preferably provided, each comprising a coated layer (106a) situated at a different location along inner surface (104a). Alternatively, as shown in FIG. 3, tray (102b) may be shaped in the form of part of a dental arch, and phosphor coated layer (106b) may comprise a portion of or the entire length thereof. Preferably, phosphor coated layer (106a), (106b) comprises at least an area suitable to obtain the image of approximately at least three teeth, although it is understood that a larger or smaller area may be desirable.

Referring to FIG. 1, tray (102) is preferably, made of, for example, hard plastic, rigid rubber, silicon, Teflon, thermoplastic material, Capron or an acrylic material. Tray (102) is preferably manufactured in a wide variety of sizes in order to fit comfortably in the oral cavity and around the teeth of a variety of patients (e.g. children and adults). Alternatively, tray (102) may be at least partially made of a flexible or elastic material, for example, rubber or soft plastic, for allowing tray (100) to conform around the teeth of a patient. Tray (102) may be inserted to a suitable disposable sterile covering prior to each use.

As described above, the system (100) of the present invention is designed to be used with a filmless radiography system. As an example, system (100) can be used as part of a filmless radiography system that is designed according to at least some of the principles of U.S. Pat. No. 3,622,785 as described herein above, which is incorporated herein by reference. Thus, according to the first embodiment of system (100), as shown in FIG. 1, the tips of a flexible fiber optic bundle (112) extend along the inner (lingual or palatal) surface (104) of tray (102), and phosphor coated layer (106) is deposited thereon. According to this embodiment, an image intensifier (not shown) is physically mounted on, and in optical communication with the fiber optic bundle (112). A camera (not shown) is preferably physically mounted on and in optical communication with the output of the image intensifier, external to the oral cavity. System (100) preferably further comprises at least a processing station comprising a computer (120) and a display unit (122).

Radiation from an x-ray source (10) impinges on phosphor coating (106) and generates a low-level, subvisual signal which is then transmitted through fiber optic bundle (112) to the image intensifier. The low-level signal is amplified by the image intensifier, and the camera picks up the signal. This signal is processed and amplified by computer (120), and displayed on monitor (122).

Alternatively, image data may be transferred wirelessly to the image intensifier using any wireless technology, for example, Bluetooth® technology, WiFi, WiMax, radio, IR, GSM, GPRS.

Figure 4:
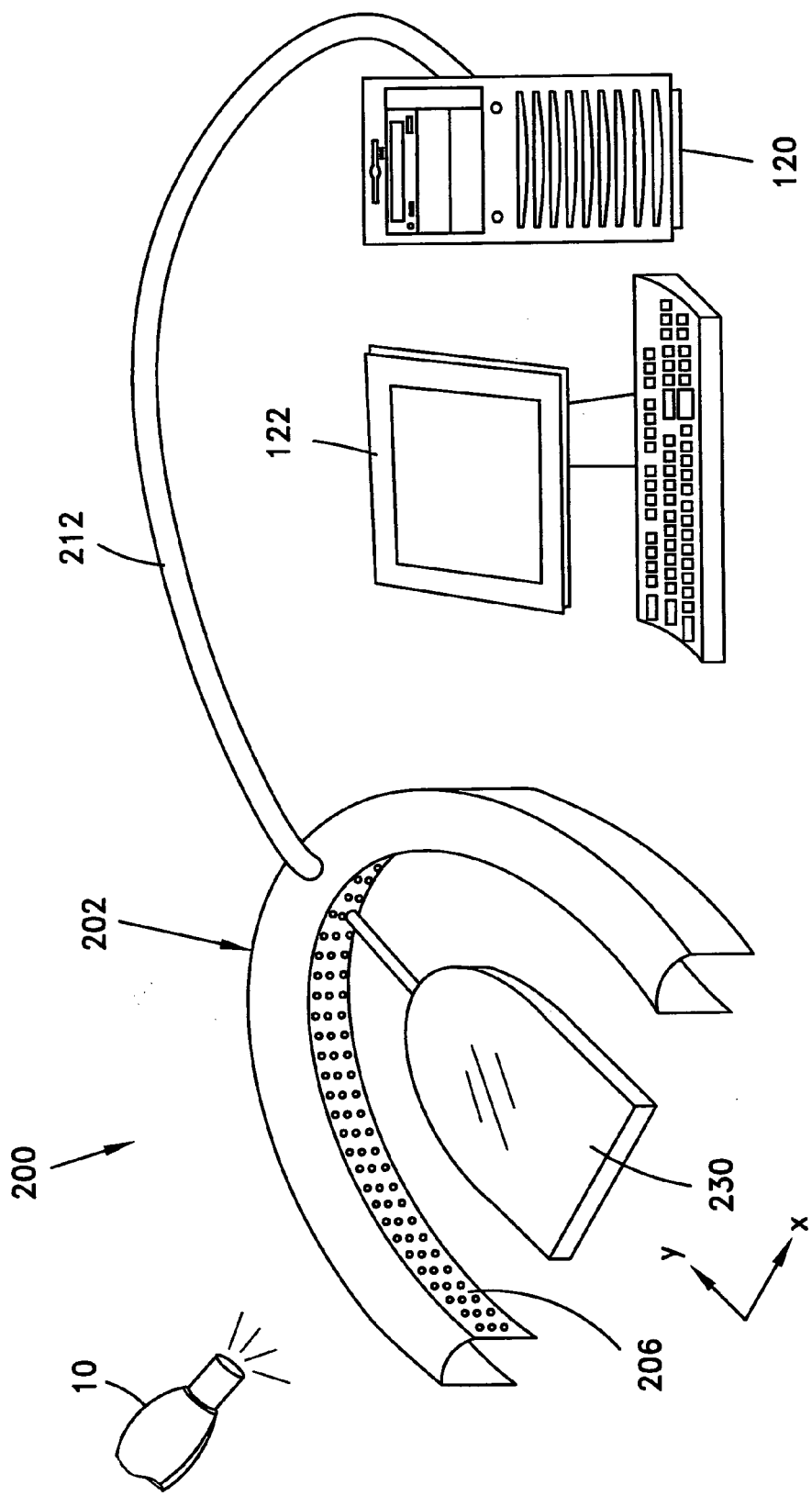
FIG. 4 illustrates the first embodiment of the intraoral digital x-ray apparatus of the present invention, wherein an optical device is utilized for gathering intraoral image data.

A second aspect of the first embodiment of the intraoral digital x-ray system (200) is shown in FIG. 4, wherein an optical device (230), for instance at least one lens or mirror, or a plurality thereof, either alone or in combination, is situated at the central portion of tray (202), and disposed above the tongue when tray (202) is situated intraorally. Optical device (230) is fixed to tray (202) via a gyroscope or gimbals apparatus, although shown in the figure schematically for the sake of clarity as merely a rod. Optical device (230) may be rotated about the x- and y-axes to change the angle accordingly, and is controlled remotely by the dental practitioner. Optical device (230) gathers image data from scintillator (206) and transfers the data to display monitor (122) accordingly.

It is understood that the elements of system (100), (200) as described herein above are merely examples of possible components that may be used to transfer the data gathered by phosphor layer (scintillator)(106), (206) to the visual display unit, and suitable alternative components may be interchanged with those specifically mentioned. Such components as well as the method of transferring the image data are well known by the man skilled in the art.

Figure 5:
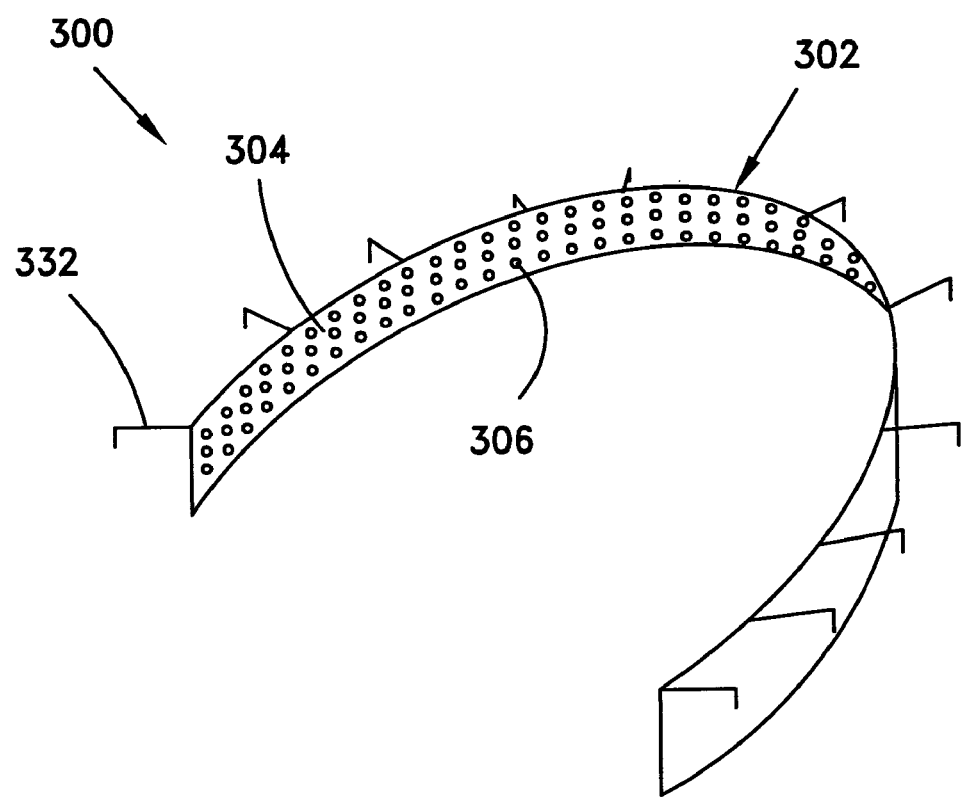
FIG. 5 illustrates the first embodiment of the intraoral digital x-ray apparatus of the present invention, wherein an image detector is an elongated strip in the form of an entire dental arch.

Referring to FIG. 5, a third aspect of the first embodiment of the intraoral digital x-ray system (300) of the present invention is shown comprising all of the features of the first embodiment as described herein above, with the following differences. System (300) comprises an elongated curved strip (302) in the shape of an entire dental arch. The surface (304) of strip (302) comprises an image detector in the form of a phosphor coated layer (306) around the entire length of the arch. Strip (302) is shown in the figure positionable on the lingual side of teeth of the lower dental arch, although it is understood that layer (306) may be similarly molded to be positioned on the lingual side of teeth of the upper dental arch (not shown). Strip (302) is preferably made of a shape memory material that constantly tries to return to the straightened shape. Thus, when reshaped to fit around the teeth of the patient, the inside of the dental arch presses tightly against the lingual (or, palatal) teeth due to its "desire" to return to a straight line.

According to the third aspect, securing means are provided for temporarily securing strip (302) within the oral cavity. One example of securing means is shown in FIG. 5 in the form of a hook (332) which is disposed over teeth to allow strip (302) to hang over the lingual surface of the teeth. Alternative or additional securing means may include providing an adhesive surface to the back face of strip (302) for temporarily adhering to teeth.

Alternatively, although strip (302) is shaped in the form of an entire dental arch, phosphor coated layer (306) may comprise only a portion of the length of the dental arch. Alternatively, layer (302) may be shaped in the form of part of a dental arch, and phosphor coated layer (306) may comprise a portion of or the entire length thereof.

According to the third aspect (300) image data may be transferred wirelessly or via a cable (not shown) as described herein for the first aspect (100).

Thus, the present invention provides an intraoral x-ray system (100), (200), (300) comprising a tray that may be comfortably situated within the oral cavity of a patient, and allows the image of at least part of the dental arch to be displayed electronically without requiring expensive electronics to compensate for and/or correct image distortion. System (100), (200), (300) does not require skill of the dental practitioner to operate or place in the oral cavity. Moreover, there is no need to remove and replace and/or reposition system (100), (200), (300), which conventionally would cause discomfort to the patient.

Figure 6:
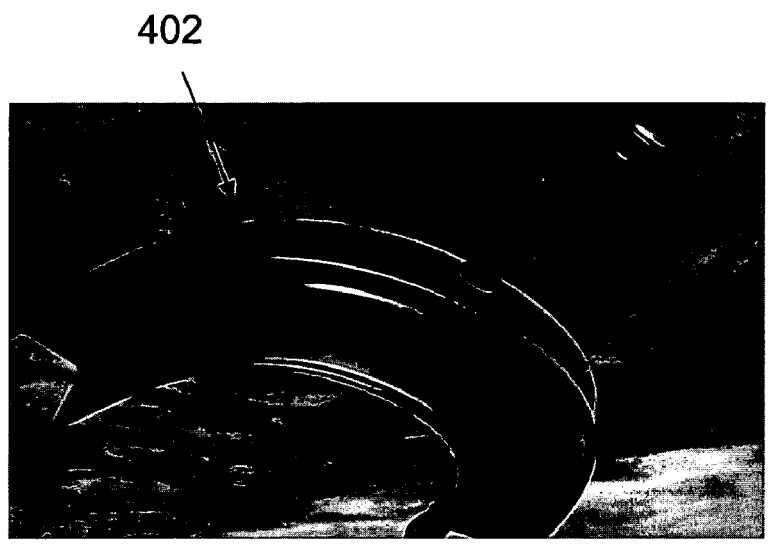
FIG. 6 illustrates a bottom perspective view of the second embodiment of the dental tray of the present invention.

Referring to FIG. 6, a second embodiment of the present invention is shown in a bottom perspective view, comprising an anatomically designed dental tray (402) in the shape of a dental arch, and utilizes indirect digital dental radiology based on a photo-stimulated luminescence process to display intraoral images. According to one aspect of the second embodiment, image detectors in the form of x-ray storage plates comprised of polycrystalline phosphor are used, wherein there is no immediate fluorescent effect until visible/UV/IR light radiation is applied to the phosphor, as described herein below.

For the sake of clarity, the terms "phosphor plate" and "storage plate", and other combinations thereof are used herein interchangeably, and refer to the plate comprised of the polycrystalline phosphor material that absorbs the x-ray radiation. Further, for clarity, it should be emphasized that the term, "phosphor" as used herein does not refer to the chemical element, rather to a material that exhibits properties of phosphorescence.

It should be noted that although the description of the second embodiment is in terms of the polycrystalline phosphor material, other phosphors or scintillators, or any other material or elements that has the characteristics described herein (e.g., silicon) may be utilized, mutatis mutandis.

Figure 7:
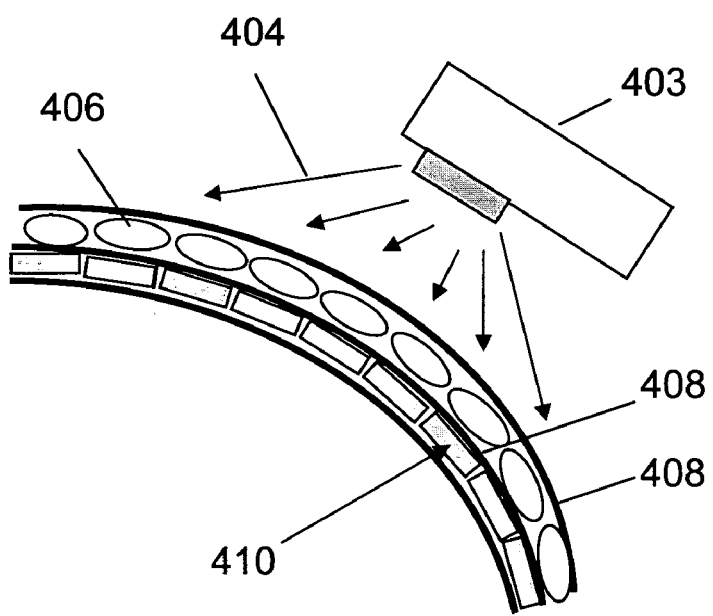
FIG. 7 illustrates a schematic view of the x-ray procedure performed using the tray of the second embodiment.

The indirect digital dental radiology process was referred to briefly herein above, and is described in more detail with reference to the present invention, herein below. Shown schematically in FIG. 7, an x-ray source (403) emits x-ray radiation, indicated by arrows (404). The x-rays (404) first pass through the substrate material (408), i.e. the material comprising the tray of the invention, which functions essentially as a holder for a plurality of X-ray storage radiation plates (410), as described herein below. X-rays (404) then pass through the photographed teeth (406), and then another layer of the substrate material (408). The substrate material (408) has low absorption of X-rays (404). When X-Rays (404) enter storage radiation plates (410) a high amount of absorption occurs on electron "color centers" (i.e. when in crystal structures some ions are replaced by electrons, causing non-periodic artificial defects), and in this way is held by the phosphor plates for very long time, since the polycrystalline phosphor is very stable. The life-time of the material is limited only by its mechanical integrity.

Each tray (402) comprises preferably one phosphor plate, but optionally more than one plate, forming an elongated screen (or row of plates), for allowing the dental practitioner to obtain an image of at least part of the dental arch.

Until the reading of the storage radiation plates is performed, an opaque covering, such as a disposable black nylon (not shown) protects the color centers from losing the stored energy. The nylon covering is preferably a disposable hygienic bag or sleeve that is positioned around the tray for insertion to the patient's mouth. The energy can be freed by being exposed to visible light when the nylon covering is removed. This is accomplished during the reading stage of the process, described herein below.

In order to read the picture that is stored in the "memory", the polycrystalline phosphor within the tray is scanned with low power diode laser focused light, according to the present invention. The read-out is performed by means of a high sensitive Photo-Multiplier Tube (PMT) detector element, described herein below. During this reading process the picture is stored digitally. Simultaneously, the information on the polycrystalline phosphor is erased, and it is ready to store another image. An image can be produced and erased an infinite number of times.

To read the storage radiation plates, a small standard photodiode in a red spectral band is preferably used in the laser scanner according to the present invention. The radiation emitted by the laser destroys the "color centers" produced by the x-rays, and stimulates emission of radiation in a visible wavelength, different than that of the stimulated wavelength.

The scanning laser focuses on the storage radiation plates, along an area that corresponds to the required spatial resolution. The resulted fluorescent light is collected by the Photo-Multiplier detector, which produces an analog signal as a function of the scanning time. This output is translated into a digital signal, and is then processed by a computer.

Preferably, the scanning laser intensity is 1-3 mW in a 630-670 nm wavelength range (red).

The scan reading time according to the present invention is preferably nearly 1 μSec per resolution pixel. The reading time depends on the dimensions of the storage plate. According to one aspect of the present invention, for a storage screen comprising half of a dental arch, having dimensions of approximately 50 mm×20-25 mm (length×height), where the resolution is 50 μm, the number of resolution pixels is $2 \times 10^5$, the reading time is equal to approximately 0.2 sec. This means that the reading time will be limited not by the physical capability of the process, but by the velocity of the scanner. The cost of the scanner is at least partially a function of the velocity of the scanner. Preferably, the scanner is capable of performing a scanning of one plate every 5 seconds.

The scanner preferably comprises a PMT detector (including power supply and lens), an X-Y scanner (including drivers and optics), a red diode laser, and Data acquisition software (including sync, power supply, and driver electronics).

The scanner dimensions are preferably approximately 12 cm×12 cm×12 cm, which is much more compact than prior art scanners for indirect digital radiaography.

According to one aspect of the present invention, parameters of the reading camera may include: nearly 1 Mega pixel; Resolution—20 μm (without the need for relay lenses); Scan rate 5 sec/frame for simple scanner. Scan time can be lowered for higher scan laser intensity.

The scanner is connected to a display unit for displaying the image. Alternatively, the scanner comprises an integral display unit. The tray of the present invention may be connectable to the scanner via a USB connection. Optionally, scanner has email capabilities for transferring images via email. According to the present invention, a costly computer, which reduces the maneuverability of the entire system, is not required for the present invention. Thus, the present invention comprises a mobile scanning system that may be transferred between rooms in a dental office with ease.

Figure 8:
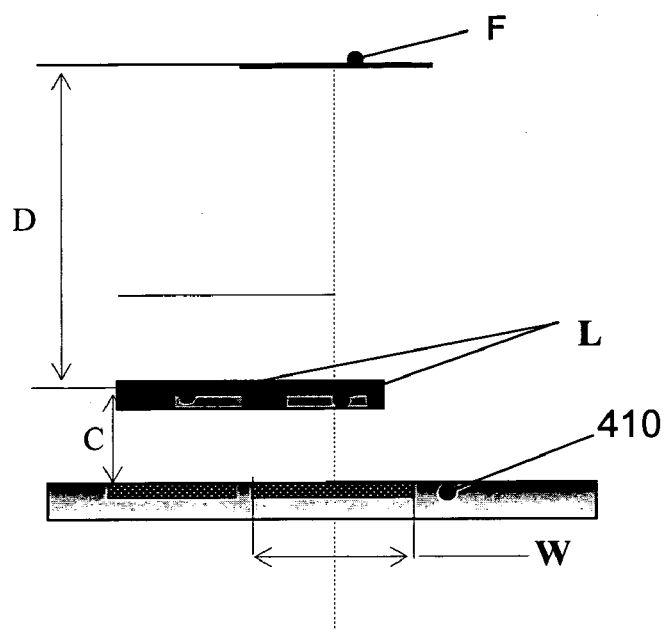
FIG. 8 illustrates a schematic view of the essential components of the second embodiment of the present invention, and their relative distances between each other.

The geometrical limitation of the system of the present invention for X-ray image spatial resolution W is described below, with reference to FIG. 8 and the equation:

$$W=L(C/D+1)+C/DF$$

Wherein,
L=the linear length of the object (the tooth) that must be resolved;
C=the distance between the tooth and the storage plate;
D=the distance between the x-ray camera to the tooth plane; and,
F=the x-ray source spot diameter.
When
L=0.02 mm;
C=10 mm;
D=400 mm; and,
F=0.1 mm.
Then, W=0.02 mm.

Since the scanning area is not big (e.g., nearly 5 cm$^2$), the scanner may be designed with main optics only, without the relay optics, which, thereby reduces the manufacturing costs significantly.

In the reading stage, the activated color centers are destroyed by means of visible (red, for example) light, and during the recombination of free electrons a spectrally short wavelength (blue) radiation is observed. This blue radiation is recorded by a high sensitive analog detector.

The quantum efficiency of the process can reach up to 70%. When energy is high, the material through which it passes naturally has lower absorption. According to the present invention, the lower absorption can be compensated by increasing the thickness of the polycrystalline phosphor. Such an adjustment is not possible with any other phosphors, including with phosphor used by Gendex, which is limited in maximum thickness to 0.3 mm. The reason for this limit in the Gendex phosphor is that it is powder-based, as described herein above. Thus, for greater thicknesses the light scattering during the scanning process gets too high, and as such, a lot of light is lost. Moreover, this scattering reduces the spatial resolution. In the present invention, phosphor plates are manufactured thicker, for better efficiency at higher X-ray energy levels. This allows very low scattering and absorption in visible spectral range.

The sensitivity and signal-to-noise ratio of the system of the second embodiment are limited by the properties of the polycrystalline phosphor during the recording process and by sensitivity of the detector during the reading process. The usage of the PMT detector allows X-Ray energy levels to be lower than usually used for dental applications. Alternatively, shorter radiation time may be allowed, which is an important advantage for all kinds of x-ray systems. The usage of PMT detectors allow nearly 20 db of dynamic range to be reached for the resulted digital pictures (i.e. a contrast of nearly 100 between the most dark and the brightest spots on the picture).

The PMT detects light power, and gives an output analog signal as a function of the scan time. This signal is translated into digital and is processed for: contrast enhancement; spatial frequency enhancement; and, subtraction of dark (noise) image for improving of Signal-to-Noise ratio, and taking into account of X-ray source radiation non-uniformity.

Prior art readers (scanners) used in indirect dental radiology are large and bulky, as well as very costly. Some can cost tens of thousands of dollars. According to the present invention, due to the inexpensive components that comprise the scanner, cost is reduced significantly. This enables dental practitioners who would normally be reluctant to purchase the indirect dental radiology equipment due to the expenses involved, to enjoy the benefits and advantages of indirect dental radiology.

The tray that holds the storage radiation plates is made from a substrate material preferably manufactured from RTV, because of its elastic properties as well as high resistance to a wide range of temperatures and chemicals. Biocompatible plastics, like Poly-Acrylats, Plycarbon, or Olefins can also be used as substrate material. In any case the substrate material must be opaque for obstructing visible light from passing therethrough.

One of the most important aspects of the present invention is the shape of the tray. The shape of the tray of the present invention corresponds to the shape of at least part of the dental arch, for covering the desired teeth. The cross-sectional thickness of the lingual side of the tray can be made very small, not more than 5 mm thick, which includes the storage polycrystalline plates and the substrate material. Due to the thin structure, it can be easily and comfortably fixed on the teeth, and thereby completely eliminate the gag reflex associated with traditional x-ray apparatus, as described herein above.

The polycrystalline phosphor material is situated close to the teeth being photographed on the lingual side of the teeth, and absorbs the X-rays that pass through the tooth, as described herein above. The absorption process of X-rays in the polycrystalline phosphor material of the present invention is more effective than with ordinary phosphor material. Additionally, the lifetime of the energetic excited level is long enough to read the data (picture) after any reasonable time period.

The polycrystalline phosphor is not an elastic material and can be manufactured at a thickness of 1-3 mm for optimal X-Ray absorption efficiency. According to the present invention, when the tray comprises a plurality of phosphor plates, each phosphor plate is preferably manufactured having a two dimensional cross-section of approximately the same dimensions of the two dimensional cross-section of a single tooth. Thus, according to one aspect, the dimension of each phosphor element is preferably approximately 5 mm×10 mm×1 mm (length×height×thickness). In this case, it is preferable to have two levels of plates for each tooth so that the total height is approximately 20 mm, as described herein above. Each phosphor plate is fixed at the lingual portion of the dental tray of the invention by, for instance gluing thereto. Thus, the substrate material surrounds the phosphor plates, thereby protecting from damage by intraoral fluids.

The theoretical limit for detector element pitch is 1 nm. In reality, the resolution is not limited by pitch value, but by the diameter of the focused laser beam in the scanner, which is preferably less than 50 μm (at $1/e^2$ intensity definition for Gaussian beam laser distribution). The corresponding achievable spatial resolution is nearly 20 lines per mm. It is important to note that this is not a required limit. This value is preferably used in order to make the scanner simpler, smaller and cheaper In one aspect, the resolution will be limited by scanner performance, and not by granulated phosphor resolution.

X-ray sensitivity for the phosphor material of the present invention is preferably nearly 30 eV per luminescent color center. The density of the color centers can be made very high, with a limit of reduction of dense uniformity. The final contrast of the viewable image is actually a linear function of the X-ray energy, and of the scanning laser intensity.

An important advantage of the proposed concept is that the reading process is performed outside the mouth by an external scanning reading mechanism. This means that all electronics, wires, and weight limitations are not applied at the intra-oral portion of the system. This enables the user to photograph all teeth of a dental arch by taking only one or two x-rays, without wearing away the on-tooth components. Such a separation between absolutely passive intra-oral components and scanning part with all needed electronics and interface to computer increases the overall reliability of the system.

A third embodiment of the present invention provides an anatomically designed dental tray (402) in the shape of a dental arch as described according to the second embodiment (see FIG. 6), mutatis mutandis, however, in the third embodiment, direct digital dental radiology is utilized to display intraoral images. The direct imaging system has a reduced overall sensitivity in comparison to the indirect imaging system, however, the direct imaging system is advantageous in its relative simplicity and relatively low manufacturing costs of the system components. One of the advantages associated with the dental arch shape of the present invention is that the sensors can be situated in close proximity to the teeth undergoing the x-ray, which prevents a shadow from forming on the plate. In the prior art, the flat rigid sensor plates are unable to be situated in close proximity to the teeth of the dental arch, thereby allowing a shadow to form on the plate.

Figure 9:
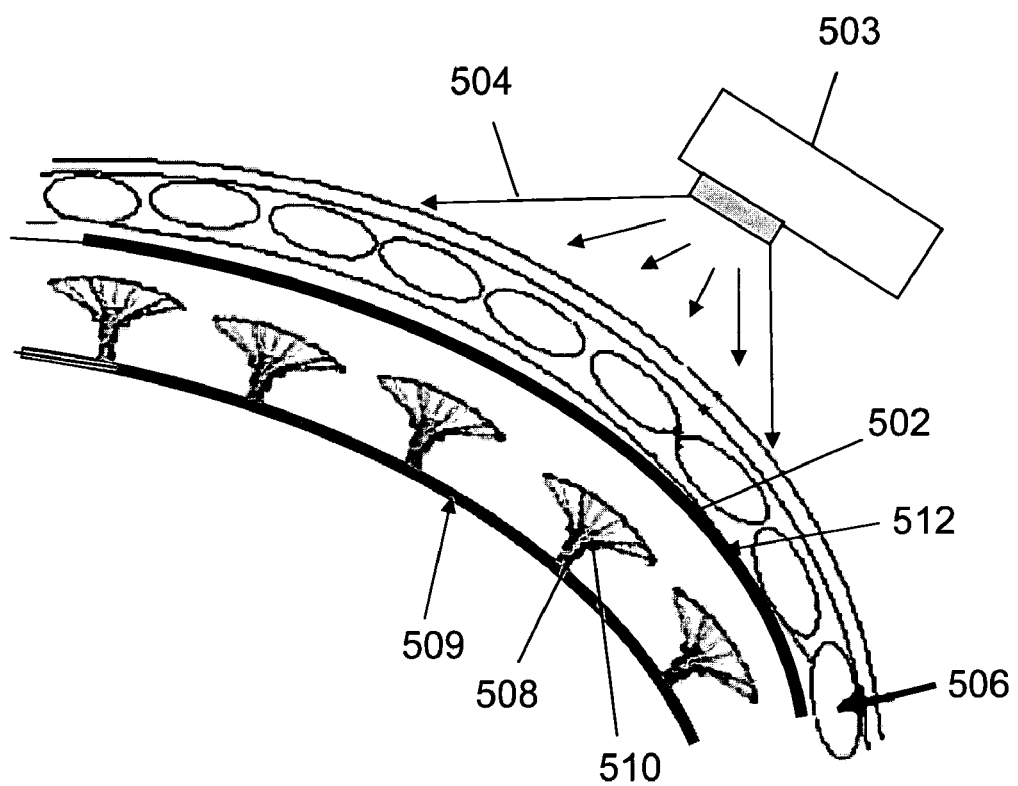
FIG. 9 illustrates a schematic view of the x-ray procedure performed using the tray of the third embodiment of the present invention.
Figure 10:
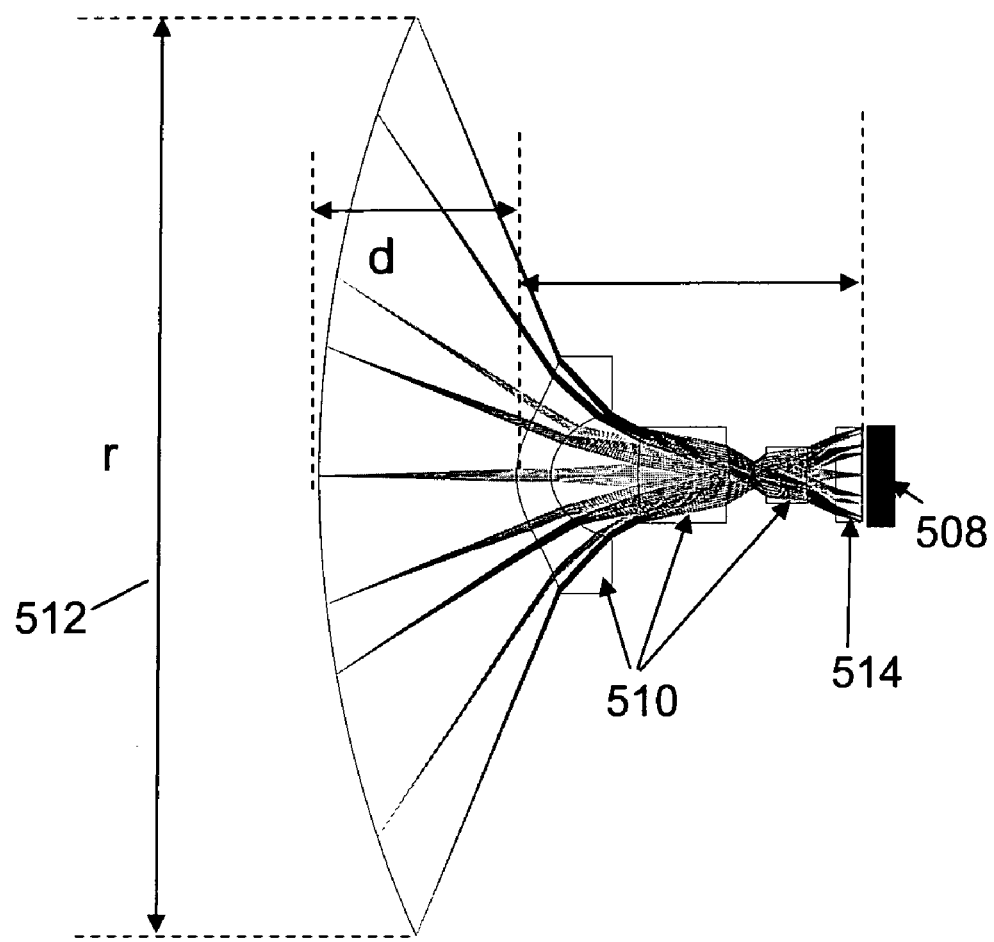
FIG. 10 illustrates a single optical arrangement of the third embodiment of the present invention.

The direct digital dental radiology process was referred to briefly herein above, and is described in more detail with reference to the present invention, herein below. Referring to FIGS. 9 and 10, in comparison with the prior art, which utilizes a single CMOS chip, the present invention provides an image detector in the form of a row (or, screen) of very small video CMOSes (508) together with very small widefield optics (510) situated at the lingual side of the tray. The optics (510) are focused on the plane of an array of scintillators (512) attached to the plastic substrate (the tray) (502) assembled thereon. The scintillators (512) are the standard processed CsI:Tl column grown type. These scintillators are used because of their high absorption efficiency of X-ray radiation. Each scintillator absorbs X-ray radiation at the relevant 30-80 Key energy, and emits visible radiation in green.

As shown schematically in FIG. 9, the assembly of the third embodiment, including the scintillators, optics and CMOS array is assembled inside an elastic RTV or plastic monolithic structure (i.e. the dental arch shaped tray). The pixilated scintillator (512) is composed of a plurality of segments. The CMOS chips are integrated on the flexible board with a printed circuit (509) on it.

The most efficient X-ray scintillator is CsI:Tl (thallium doped cesium iodide), directly deposited on the a intra-oral substrate as an array, in order to give the best optical coupling efficiency. It is most important for our case because photon flux is very low. The relatively high absorption is one of the reasons that a pixilated scintillator is preferred in this embodiment over phosphor materials. Using phosphor, the required sensitivity cannot be approached, and it is close to the required limit even for a scintillator. Another reason that scintillators are more efficient is that the thickness of the CsI can be greater when utilizing scintillators that grow in a columnar structure. The columns tend to act as light pipes, reducing the amount of light spreading in the scintillator. Thus, for example, a 600 μm CsI layer (the preferred thickness of this embodiment) can have resolution similar to a 300 μm thick rare earth phosphor. Nevertheless, phosphor materials may be alternatively used.

Referring to FIG. 10, the light generated by each scintillator (512) is directed onto the CMOS (508) active plate by its optics (510). The peak light absorption efficiency of the CMOS silicon is not in the green spectrum, but at 550 nm wavelength it is rather high, and therefore very efficient.

Scintillator columns have a nearly 50 μm diameter, which is responsible for the system's resolution limit.

According to one aspect of the third embodiment, the CMOS may be a miniature CMOS from Micron with the following specification characteristics:
Number of pixels: 256×256
Pixel size: 5.6 μm×5.6 μm
Sensitivity at 550 nm: 4 V/Lux*sec in ×1 gain
8 bit ADC resolution
SNR: 42 db The actual dimensions of this CMOS chip are very small, i.e. 1.4 mm×1.4 mm. Together with board the CMOS dimensions are 4 mm×4 mm. It is the most compact structure with reasonable resolution.

The optics proposed for this CMOS are designed to be very small, as understood from FIG. 9. According to one aspect, as shown in FIG. 10 the optics are constructed from 3 plastic lenses manufactured, for instance, by a precision injection molding process, and a narrow bandwidth filter (514) which will cut all unused wavelengths, except for the green wavelength. The optics is designed in such manner that it has very large field of view (120° as shown in the figure) in order to cover the maximum amount of tooth with single CMOS. At a distance (d) of 3 mm from the scintillator (512) output surface the linear coverage range (r) will be 10 mm for each CMOS (508), meaning that for 50 mm teeth range we need 5 CMOS with optics. The cost for manufacturing such optics is generally inexpensive when the components are purchased in large quantities, such that each CMOS plus the optics may cost a combined total of only $10.

The evaluated spatial resolution with this optics is 0.1 mm in the plane of the scintillator, which is actually the plane of the teeth because of the very close distance between them.

The F-number of the optics of the second embodiment can equal F/2. A low F-number is an important feature because of the expected lack of the efficient green light at the output of the scintillator.

A F/2 F-number corresponds to the Numerical Aperture of the lens equal to 0.25, which in turn corresponds to a 22° full plane angle of light captured by optics. The solid angle of light capture is equal to 0.11 Srad. At the scintillator output the light is spread at larger angle, nearly 30° (0.21 Srad). This means that 50% of the light is lost during the light collection process. As a result of a 20% absorption scintillator efficiency, a 20% loss inside of the scintillators, and a 20% loss on the RTV substrate and narrow bandwidth filter, nearly 30% of the whole photon energy is collected by the CMOS. X-ray photons excite the scintillator crystal in different places, and produce during this excitation nearly 10,000 green photons in each scintillator pixel. Approximately 3,000 green photons will be received by the CMOS. Taking into account that the energy of one green photon is approximately equal to $3.6 \times 10^{-19}$ Joule, and taking into account that the CMOS integration time is nearly 30 msec, and that the CMOS pixel dimensions are 5.6 µm, the required CMOS sensitivity is 0.8 lux. Such a sensitivity is on the limit of an uncooled CMOS operation in a case when all other wavelengths beside green are carefully filtered (e.g. eliminated).

The output from the CMOS can be delivered outside the oral cavity by means of electrical cable, which includes 3-4 wires for output, as well as another 2 wires for power supply of the CMOS. Alternatively, the interface may be accomplished via a wireless connection, in which the recorded picture is transferred outside the oral region by, for instance, RF. In this case the RF antenna is designed and assembled inside the tray. In the case of RF signal delivery, the RF receivers are assembled in close vicinity to the human head, and the relevant data receiving/recording system is provided. Additionally, a battery is inserted for power supply. CMOS has very low power consumption, so a small battery is sufficient. A display unit is provided to allow the image to be viewed.

According to a fourth embodiment of the present invention (not shown in the figures) the tray is manufactured having a suitable passageway or clipping elements extending along at least a portion of the lingual side of the tray, for accommodating a conventional film plate. The film plate is removably positioned through the passageway, or held by the clips, along the tray. The film plate may be suitably manufactured to fit along the tray of the invention. Alternatively, a conventional film plate may be retrofitted for use with the tray of the invention.

Figure 11A:
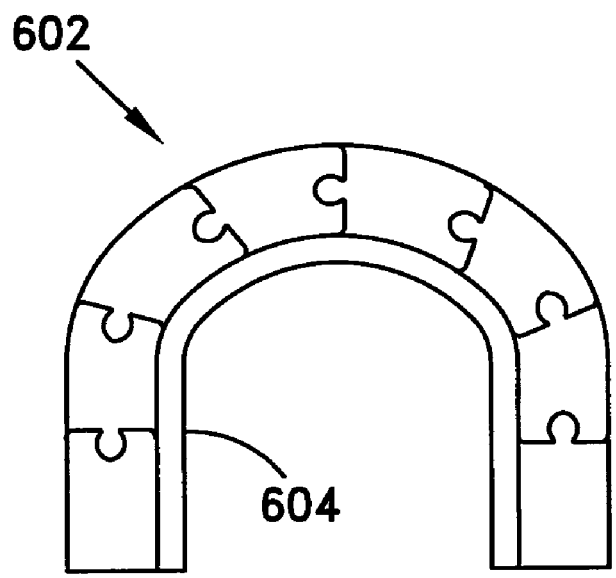
FIGS. 11a and 11b illustrate an alternative embodiment of the tray of the present invention, comprising a plurality of detachable links, in a bent position (FIG. 11a) and a straight position (FIG. 11b)
Figure 11B:
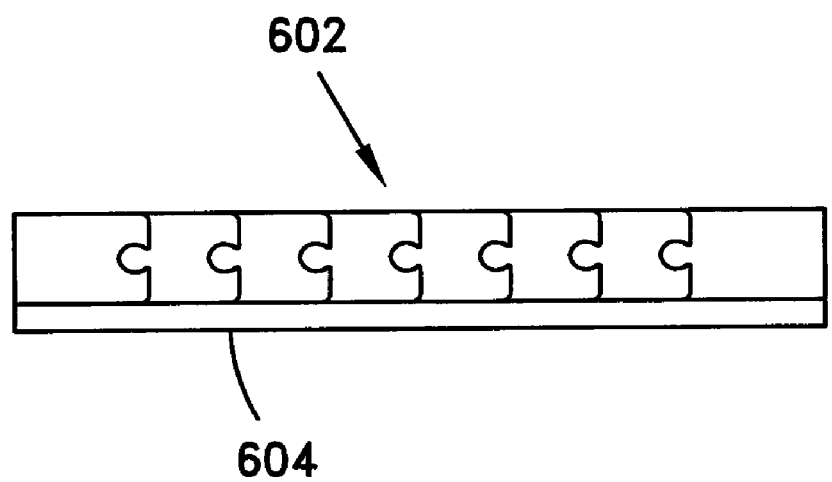

In addition to the embodiments of the tray of the present invention as described above, and shown in the figures herein, according to all embodiments, the tray may be comprised of sectional components for connecting and disconnecting to form a portion of, or an entire dental arch tray. Referring to FIGS. 11a and 11b, adjustable tray (602) is shown in a bent position (FIG. 11a) in the shape of a dental arch, and adjusted in a straightened position (FIG. 11b) for inputting to the scanner to read the plate. A film screen or row of plates is positioned within a passageway holder (604), as described herein above regarding the fourth embodiment.

Figure 12A:
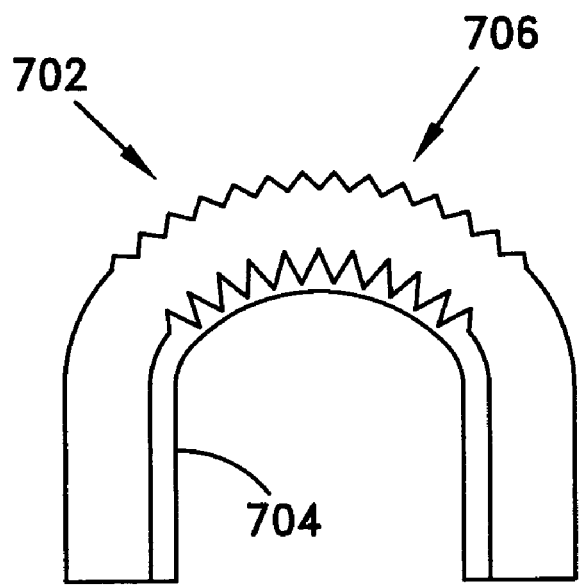
FIGS. 12a and 12b illustrate an alternative embodiment of the tray of the present invention, comprising an accordion section, in a bent position (FIG. 12a) and a straight position (FIG. 12b).
Figure 12B:
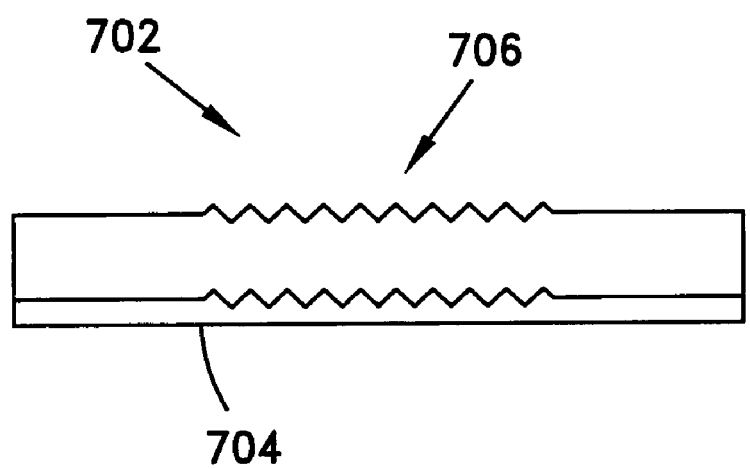

FIGS. 12a and 12b show yet another embodiment of adjustable tray (702) in a bent position (FIG. 12a) in the shape of a dental arch, and in a straightened position (FIG. 12b), comprising a holder (704) for holding a film screen or row of plates. Tray (702) comprises an accordion section (706) for bending and unbending tray (702).

Alternatively, the tray of the present invention comprises any form or bendable or adjustable material to allow the user to selectively shape the tray to a dental arch shape and an essentially straight line. In one aspect, as described herein above with respect to FIG. 5, the tray is made of a shape memory material that constantly tries to return to the straightened shape. Thus, when reshaped to fit around the teeth of the patient, the inside of the dental arch presses tightly against the lingual (or, palatal) teeth due to its "desire" to return to a straight line.

According to all embodiments and aspects described herein, the image detector may be manufactured as part of the tray, adhered to the tray, or, particularly referring to the phosphor plates, may be coated on the outer surface of the tray.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. Intraoral apparatus for obtaining undistorted digital images comprising:
   a. an arcuate dental tray securable to teeth or the gingiva of a subject, said tray configured to be in a shape of an entire dental arch;
   b. an image generating layer retained by said dental tray and having a curvature substantially identical to the curvature of said dental tray, said image generating layer being sufficiently sensitive to radiation emitted from an x-ray source and impinging thereon to generate an image which is readable by means of an image processing system.

2. The intraoral apparatus according to claim 1, wherein the dental tray comprises a lingual surface, a buccal surface, and an end surface extending from said lingual surface to said buccal surface of a sufficiently small width to ensure that the tray will be secured to the teeth or the gingiva of the subject.

3. The intraoral apparatus according to claim 2, wherein the image generating layer comprises a plurality of image detectors which are applied to the lingual or the end surface of the tray.

4. The intraoral apparatus according to claim 3, further comprising a mechanism for transferring image data generated by the plurality of image detectors to the image processing system, the image processing system being operable to convert said generated image data to a viewable image.

5. The intraoral apparatus according to claim 4, wherein the image processing system is situated externally to the oral cavity of the subject.

6. The intraoral apparatus according to claim 5, wherein the mechanism for transferring the image data comprises a fiber optic bundle.

7. The intraoral apparatus according to claim 6, wherein one end of the fiber optic bundle is situated at the lingual surface of the tray, and wherein tips of said end comprise the image detector which is chosen from any one of the group consisting of:
   a) a phosphor; and,
   b) a scintillator.

8. The intraoral apparatus according to claim 7, wherein the entire lingual surface of the dental tray comprises the phosphor or scintillator coated tips of the fiber optic bundle.

9. The intraoral apparatus according to claim 4, wherein the mechanism for transferring the image data comprises wireless technology.

10. The intraoral apparatus according to claim 6, wherein an image intensifier is in optical communication with the fiber optic bundle and a camera is in optical communication with the output of said image intensifier.

11. The intraoral apparatus according to claim 1, wherein the dental tray is an elongated strip in the shape of the entire dental arch, said elongated strip further comprises securing means for being secured to the lingual side of the teeth of the subject.

12. The intraoral apparatus according to claim 11, wherein the securing means is chosen from the group consisting of:
   a. at least one hook;
   b. at least one clip; and
   c. adhesive material.

13. The intraoral apparatus according to claim 1, wherein the image generating layer comprises one or more image storage plates held by the tray lingually to the teeth of the subject, said one or more image storage plates being used to generate an image by means of indirect digital dental radiography based on a photo-stimulated process and being chosen from one of the group consisting of:
   a. a phosphor; and
   b. a scintillator.

14. The intraoral apparatus according to claim 13, wherein the phosphor is a polycrystalline phosphor.

15. The intraoral apparatus according to claim 13, wherein the dental tray is made of a material which has a significantly lower absorption of x-rays than the material from which the storage plates are made, the tray being coverable by an opaque covering to prevent the one or more storage plates from losing energy stored thereby following absorption of the x-rays.

16. The intraoral apparatus according to claim 1, wherein the image generating layer comprises an array of one or more scintillators attached to a lingual surface of the tray, a plurality of wide field optical units focused on said array of scintillators, and a plurality of CMOS chips for generating an image by means of direct digital dental radiography.

17. The intraoral apparatus according to claim 16, wherein each of the optical units has a sufficiently wide field of view such that an entire tooth is imaged by a single CMOS chip.

18. The intraoral apparatus according to claim 1, wherein the image generating layer comprises a film plate which is removably secured to a lingual surface of the tray by means of a plurality of clipping elements.

19. The intraoral apparatus according to claim 1, wherein the tray is made of shape memory material which, when deformed during insertion into the oral cavity, is securable to the teeth of the subject by reverting to its original shape.

20. Intraoral apparatus for obtaining undistorted digital images, comprising:
   a) an arcuate dental tray, said tray configured to be in a shape of an entire, or segments of a, human dental arch and comprising a lingual surface, a buccal surface and an end surface extending from said lingual surface to said buccal surface of a sufficiently small width to ensure that said tray will be secured to the teeth or the gingiva of a subject;
   b) an image generating layer retained by said dental tray and having a curvature substantially identical to the curvature of said dental tray, said image generating layer comprising a plurality of image detectors which are applied to the lingual or the end surface of said tray and being sufficiently sensitive to radiation emitted from an x-ray source and impinging thereon to generate an image which is readable by means of an image processing system; and
   c) an optical device provided with said tray and which is capable of being rotated about x and y-axes and which is controlled remotely, for gathering image data from said plurality of image detectors and for transferring said data to said processing system.

21. The intraoral apparatus according to claim 20, wherein the optical device is chosen from the group consisting of:
   a) at least one lens;
   b) at least one prism;
   c) at least one mirror; and
   d) a combination thereof.

22. Intraoral apparatus for obtaining undistorted digital images, comprising:
   a) an arcuate dental tray securable to teeth or the gingiva of a subject, said tray configured to be in a shape of an entire, or segments of a, dental arch; and
   b) an image generating layer retained by said dental tray and having a curvature substantially identical to the curvature of said dental tray, said image generating layer being sufficiently sensitive to radiation emitted from an x-ray source and impinging thereon to generate an image which is readable by means of an image processing system,
   wherein said image generating layer comprises one or more image storage plates held by said tray lingually to the teeth of a subject, said one or more image storage plates being chosen from one of a phosphor and a scintillator and used to generate an image by means of indirect digital dental radiography based on a photo-stimulated process,
   wherein said image processing system comprises a mobile laser scanner for causing said one or more storage plates to generate fluorescent light which is indicative of the image, a photo-multiplier detector for collecting the generated fluorescent light and converting the same into an analog signal as a function of the scanning time, and means for converting said analog signal to a digital signal and for processing said digital signal.

23. The intraoral apparatus according to claim 22, wherein the dental tray is adjustably bendable between a dental arch shape and an essentially straight line for inputting information to the scanner.

24. Intraoral apparatus for obtaining undistorted digital images, comprising:
   a) an arcuate dental tray securable to teeth or the gingiva of a subject, said tray configured to be in a shape of an entire, or segments of a, dental arch; and
   b) an image generating layer retained by said dental tray and having a curvature substantially identical to the curvature of said dental tray, said image generating layer being sufficiently sensitive to radiation emitted from an x-ray source and impinging thereon to generate an image which is readable by means of an image processing system,
   wherein said tray comprises a plurality of connectable and disconnectable segments, which when connected together form a portion of, or an entire dental arch shaped dental tray.

25. The intraoral apparatus according to claim 24, wherein each of the plurality of segments is made of shape memory material which, when deformed during insertion into the oral cavity, is securable to the teeth of the subject by reverting to its original shape.

* * * * *